United States Patent [19]

Kanall

[11] 4,020,843

[45] May 3, 1977

[54] MALE EXTERNAL URINARY CATHETER

[76] Inventor: Leone Kanall, 49 Payson St., Winthrop, Mass. 02152

[22] Filed: Jan. 12, 1976

[21] Appl. No.: 648,530

[52] U.S. Cl. .................................. 128/295; 4/110
[51] Int. Cl.² ...................................... A61F 5/44
[58] Field of Search ............... 128/295, 294, 2 F; 4/112, 113, 110, 119; D83/1 U

[56] References Cited

UNITED STATES PATENTS

| 1,273,480 | 7/1918 | Griffith | 128/295 |
|---|---|---|---|
| 1,386,696 | 8/1921 | Fishback | 4/110 |
| 1,440,765 | 1/1923 | Buckley | 4/110 |
| 3,306,296 | 2/1967 | Moss | 128/295 |
| 3,394,703 | 7/1968 | Orgel | 128/295 |
| 3,604,424 | 9/1971 | Windom | 128/295 |

FOREIGN PATENTS OR APPLICATIONS

| 221,534 | 6/1909 | Germany | 128/295 |

*Primary Examiner*—Stephen C. Pellegrino
*Assistant Examiner*—Michael H. Thaler
*Attorney, Agent, or Firm*—William Nitkin

[57] ABSTRACT

A male external urinary catheter having a sheath member through which a penis is inserted, a platform upon which the penis rests having drainage openings to a lower well compartment with a funnel member draining the lower well compartment to a drainage tube.

8 Claims, 4 Drawing Figures

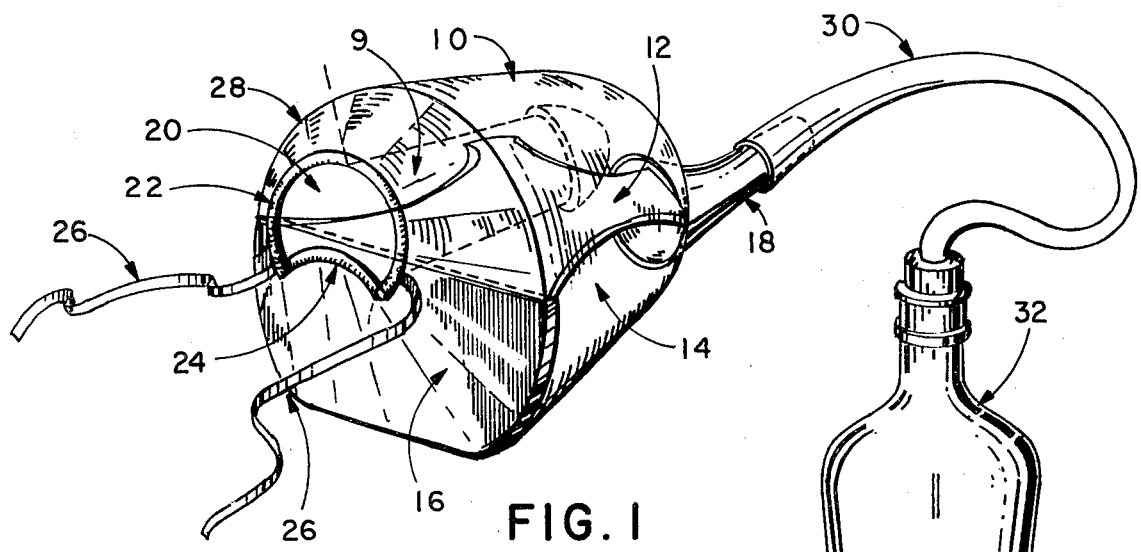
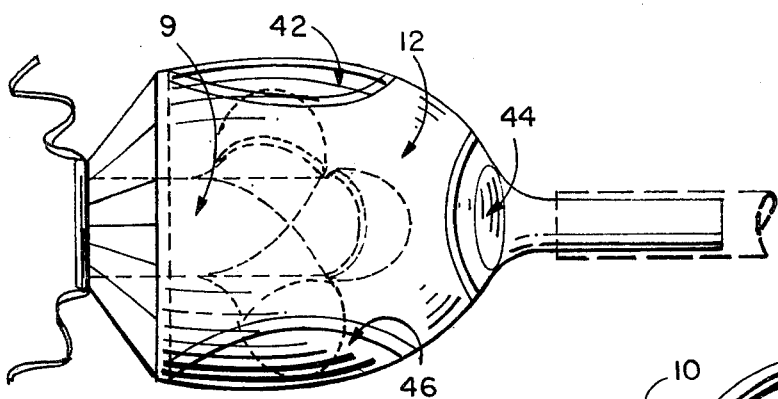
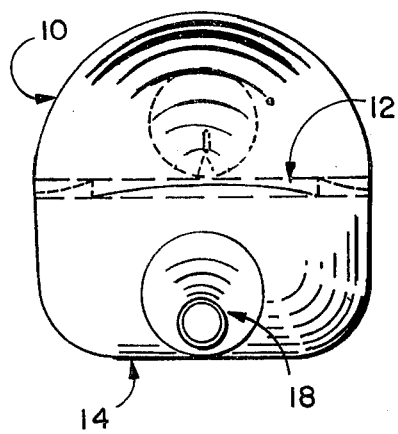
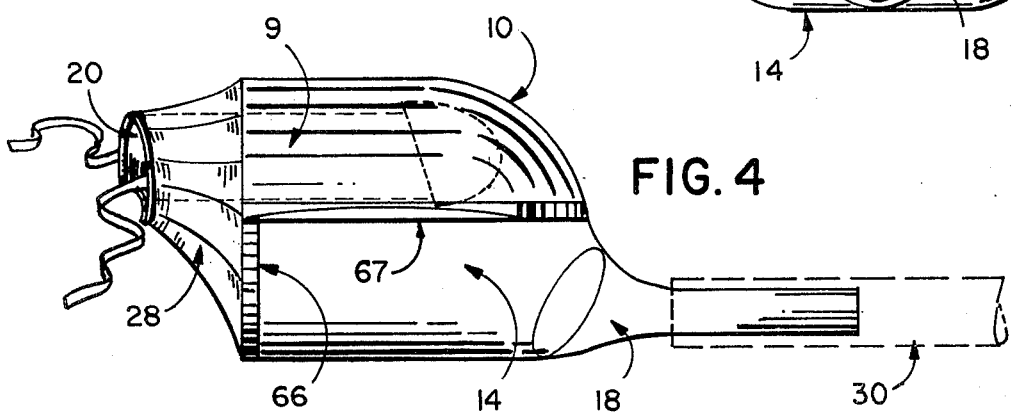

MALE EXTERNAL URINARY CATHETER

BACKGROUND OF THE INVENTION

1. Field of the Invention

This invention relates to a male urinary catheter for the evacuation and transmission of urine for use by incontinent individuals utilizing an external catheter bag having a platform therein for supporting the male genital organ to prevent the penis from coming in contact with urine voided.

2. Description of the Prior Art

There are many male external urinary catheters on the market today, such as the "Texas" catheter and the "Navy" catheter. The usual structure of these catheters is that they possess a sheath-like member which covers the penis and they are held in position on the patient by an adjustable band. An exit tube for urine voided is located at the end of this sheath member. Although in widespread use, the present art is not without its shortcomings. First, when voiding takes place, urine inevitably backs up into the sheath member causing serious infection and/or urine burns if the urine is not cleaned off the patient soon after it is voided. Moreover, the end of the sheath can easily twist preventing drainage, thereby causing the urine to back up immediately and leakage can occur at the upper end of the sheath causing great discomfort and embarrassment to the patient. In use the adjustable strap holding the sheath to the penis can have a tourniquet effect and be physiologically dangerous because of venous constriction which can cause edema. The physician treating an incontinent male patient has the choice of using either an internal catheter or an external catheter. Internal catheters are used far less frequently than external catheters because internal catheters have a higher incidence of infection and patients must be administered antibiotics concurrently with the utilization of internal catheters.

The device of this invention has been developed to provide a male external urinary catheter that is comfortable, functional, and hygienic and which eliminates the problems associated with external catheters presently on the market.

SUMMARY

The device of this invention overcomes the aforementioned disadvantages of male external urinary catheters currently on the market by utilizing a new and novel structure. The catheter of this invention consists of a casing of soft, rubber-like material, stiffened in parts that is egg-shaped with a platform affixed within on which the penis rests. Along three sides of this platform are drainage openings for the urine to run off into a lower well compartment. At the front end of this lower well compartment is a funnel member attached to a standard drainage tube which leads to a drainage bottle or bag. The catheter is held to the patient by a rubber strap which can be affixed to a belt around the patient's body. The drainage openings around the platform are located along the front and adjacent sides of the platform assuring that no matter what position the patient may be in, the urine will drain away from the penis. The bottom floor of the lower well compartment is flat and rests on the body, and the lower well compartment forms a graduated sink area leading to the funnel member. The funnel member can be of a standard approximate 2-inch length which will fit into the drainage tubes utilized by most hospitals, nursing homes, and other institutions. The catheter can be made in a variety of sizes to accommodate individual differences in anatomy. Since an important object of this invention is to drain urine from the platform, the platform can be made of, or covered by Teflon or other hydrophobic material to which liquid will not adhere. Urine drainage passes from the front end of the lower well compartment, through the funnel member and into the drainage tube which leads to a bottle or bag. It should be noted that even if there is some back up of the urine due to a twisting or constriction of the drainage tube, the urine will back up only to the lower well compartment and will not make contact with the penis. Further, this catheter eliminates the problem of the twisted catheter end whereby no urine exits the drainage tube at all causing urine back up against the patient. In the device of this invention, the top dome of the catheter and the base are made of a firm rubber-like material which will not twist or be deformed by the movement of the patient. The section of the catheter affixing to the base of the penis is of soft pliable rubber-like material conformable to individual differences in anatomy. The outer shape of the catheter in one embodiment is egg-shaped, but the shape can also be more circular, the more circular embodiment being more suitable for the more active patient. A further object of the invention is to provide a sturdy device which can be reused if cleaned or disposed of.

BRIEF DESCRIPTION OF THE DRAWINGS

FIG. 1 is a three-quarters perspective view of the device of this invention showing a penis in outline form resting on the platform, associated drainage tube and bottle member.

FIG. 2 is a top view of the device of this invention showing more clearly the internal structure of the platform with its drainage openings and a penis in outline form in various positions on the platform.

FIG. 3 illustrates a front end view of the device of this invention showing the funnel member attached to the lower well compartment.

FIG. 4 is a side view of the device of this invention showing a penis in outline form in position on the platform, the lower well compartment, funnel member and drainage tube attached thereto.

DESCRIPTION OF THE PREFERRED EMBODIMENT

For ease of illustration the device of this invention has been illustrated as being transparent so that it inner structure may be seen. It should be noted that the device of this invention can be made of both opaque or transparent rubber or synthetic materials, but that a transparent catheter has the advantage that a doctor or nurse can easily see whether the catheter should be cleaned or replaced.

FIG. 1 shows the apparatus of this invention wherein an outlined penis 9 is shown resting on platform 12 below upper portion of casing 10. This platform separates the penis from lower well compartment 14 which communicates with funnel member 18 which is attached to drainage tube 30 which carries the urine to drainage bottle 32. Equivalent drainage tubes and bottle combinations can also be utilized. At the rear of lower well compartment 14 is baffle 16 which prevents the urine, once it has drained into lower well compartment 14, from backing up into opening 20 through which the penis is inserted. This opening is within sheath member 28 which is shown in a fully extended position but which is composed of a soft, compressible material enclosing the base of the penis as it rests on platform 12, yet conformable to the anatomical differences of individuals. At the base of opening 20 is slight indentation 24 to enable the device to fit the male anatomy. Affixed to the perimeter of opening 20 are straps 26 to hold the device of this invention to the patient.

FIG. 2 illustrates a top view of the device of this invention showing penis 9 in outline form resting on platform 12 in various positions. Platform 12 is affixed to the sides of the catheter and has three drainage openings defined by the shape of platform 12. Drainage openings 42 and 46 are on the sides of platform 12 and drainage opening 44 is at the front of platform 12. In one embodiment of this invention it has been found that having the edges of the platform that form the drainage openings slope downward slightly causes better drainage of the urine. Also, this platform can be covered by Teflon or hydrophobic material so as to quickly disperse any urine that may rest thereon.

FIG. 3 is a front end view of the device of this invention showing funnel member 18 attached to the front end opening of lower well compartment 14. Also illustrated are platform 12 with a penis in outline form shown resting thereon and showing upper and lower portions of casing 54.

FIG. 4 illustrates a side view of the device of this invention wherein penis 9 in outline form is shown resting on platform 12 within upper casing 10. Opening 20 through which the penis is inserted is shown in a displaced position. Sheath 28 composed of soft, compressible rubber or synthetic material is illustrated in an extended position. Also seen is baffle 16 which prevents urine from backing up into sheath 28 from lower well compartment 14. Funnel member 18 and drainage tube 30 can be constructed of a stiffened material that will not twist in any way and cause a back up of urine. Drainage tube 30 is shown leading out of the illustration. It should be noted that sheath 28 can also be affixed to the patient by a variety of means after the penis is inserted through opening 20 of sheath 28. Although the more standard adjustable band can be used, it is felt that in the preferred embodiment of the device of this invention such constriction should not be placed around the penis and that strap members, such as straps 26 in FIG. 1, should be utilized. Such strap members are common in the art and extend to a rubber belt encircling the waist of the wearer and are affixed thereto by buttons or other equivalent fastening means.

Although the present invention has been described with reference to particular embodiments, it will be apparent to those skilled in the art that variations and modifications can be substituted therefor without departing from the principles and spirit of the invention.

I claim:
1. A male external urinary catheter comprising:
a truncated sheath member having on one end an opening through which a penis is adapted to be inserted, said opening being capable of encompassing the base of the penis;
an elongated casing, affixed about the perimeter of the other end of said sheath member, said casing having a large opening in the upper portion thereof in the end adjacent said sheath member to receive the penis therethrough;
a platform intermediately disposed within said casing, and positioned in alignment with the lower extent of said upper casing portion opening, upon which said penis is adapted to rest after insertion said platform acting to further partition an enclosed lower well compartment within said casing, said platform having a series of drainage openings between itself and the casing sides;
a funnel member affixed to an aperture within the base of said lower well compartment; and
means for affixing said catheter to the body of the patient.

2. An apparatus as described in claim 1 further including means for draining said lower well compartment comrpising a drainage tube affixed to said funnel leading and connected to a urine container.

3. An apparatus as described in claim 1 wherein the means for affixing said apparatus to the patient includes straps attached to the perimeter of said sheath member opening.

4. An apparatus as recited in claim 1 wherein said platform has incorporated within its surface structure hydrophobic material to repel urine which may fall upon it.

5. An apparatus as recited in claim 1 wherein the edges of said platform forming drainage openings slope downward to assist in the drainage of urine into said lower well compartment.

6. An apparatus as recited in claim 1 wherein said sheath member portion surrounding said opening is pliable and includes a lower recessed portion to conform to the lower base of the penis of the male anatomy.

7. A male external urinary catheter comprising:
an oblique casing, of the type substantially similar to an elliptic paraboloid having a flattened lower base surface, having a first casing end of a substantially circular nature;
a platform intermediately disposed within said casing, being in a parallel plane with said flattened lower base surface, having a series of drainage openings therein about its edges abutting said casing, said platform partitioning an upper casing portion and an enclosed lower well area;
the upper portion of said first circular casing end being, above said platform, a semi circlar opening to receive a penis whereby said penis may rest upon said platform, said casing and being enclosed below said platform;
a sheath extending about the circumference of said first casing end and being affixed thereto narrowingly radiating to an adjustable opening through which said penis may be inserted to rest upon said platform, said opening encompassing the base of said penis; and
means for draining said casing lower well compartment.

8. An appratus as described in claim 7 wherein said means for draining said lower well compartment includes an aperture therethrough substantially positioned at a second casing end and a funnel incorporated therewith.

* * * * *